United States Patent [19]

Carpentier et al.

[11] Patent Number: 4,790,843

[45] Date of Patent: Dec. 13, 1988

[54] PROSTHETIC HEART VALVE ASSEMBLY

[75] Inventors: Alain Carpentier, Paris, France; Ernest Lane, Huntington Beach, Calif.

[73] Assignee: Baxter Travenol Laboratories, Inc., Deerfield, Ill.

[21] Appl. No.: 874,618

[22] Filed: Jun. 16, 1986

[51] Int. Cl.$^4$ .............................................. A61F 2/24
[52] U.S. Cl. ...................................................... 623/2
[58] Field of Search ............................................ 623/2

[56] References Cited

U.S. PATENT DOCUMENTS

| | | |
|---|---|---|
| Re. 31,040 | 9/1982 | Possis ...................................... 623/2 |
| 3,898,999 | 8/1975 | Haller . |
| 3,997,923 | 12/1976 | Possis . |
| 4,078,268 | 3/1978 | Possis . |
| 4,211,325 | 7/1980 | Wright . |
| 4,233,690 | 11/1980 | Akins . |
| 4,259,753 | 4/1981 | Liotta et al. . |
| 4,506,394 | 3/1985 | Bedard . |
| 4,680,031 | 7/1987 | Alonso ...................................... 623/2 |

OTHER PUBLICATIONS

"Anatomic Analysis of Removed . . . 1980 to 1983", *Human Pathology*, Frederick J. Schoen, M.D., PhD, et al, vol. 16, No. 6 (Jun. 1985), pp. 549-559.

"The Bjork-Shiley Mitral Valve", Viking O. Bjork, M.D., et al, *The Annals of Thoracic Surgery*, vol. 18, No. 4 (Oct. 1974), pp. 379-390.

*Primary Examiner*—Richard J. Apley
*Assistant Examiner*—James Prizant
*Attorney, Agent, or Firm*—Gordon L. Peterson

[57] ABSTRACT

A prosthetic heart valve assembly which includes an artificial annulus, a prosthetic valve and a retaining ring for releasably retaining the prosthetic valve on the artificial annulus. By removing the retaining ring, the valve can be replaced with another valve. The artificial annulus includes a suture ring and a mounting ring mounted on the suture ring for receiving the prosthetic valve and the retaining ring.

17 Claims, 3 Drawing Sheets

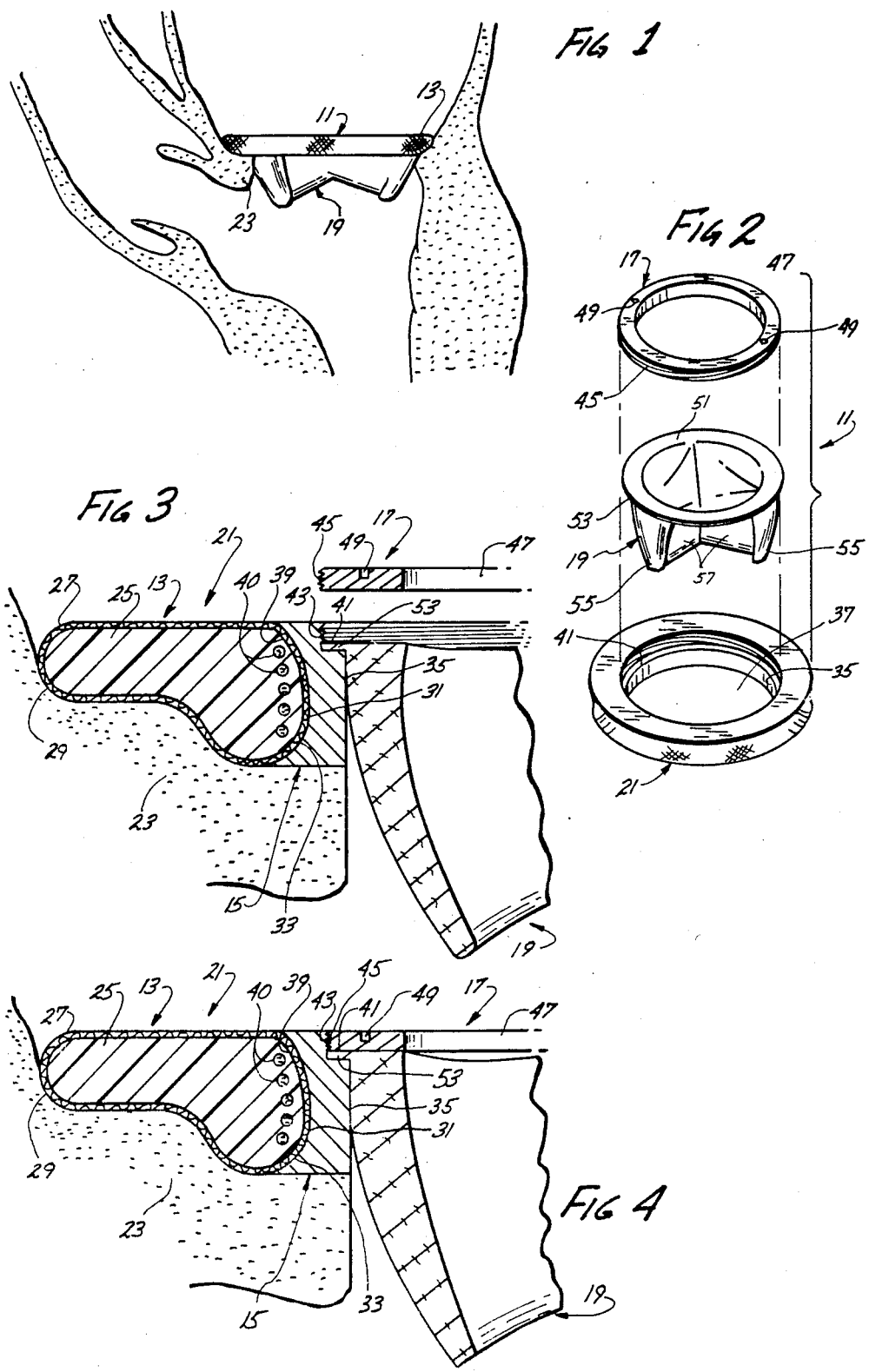

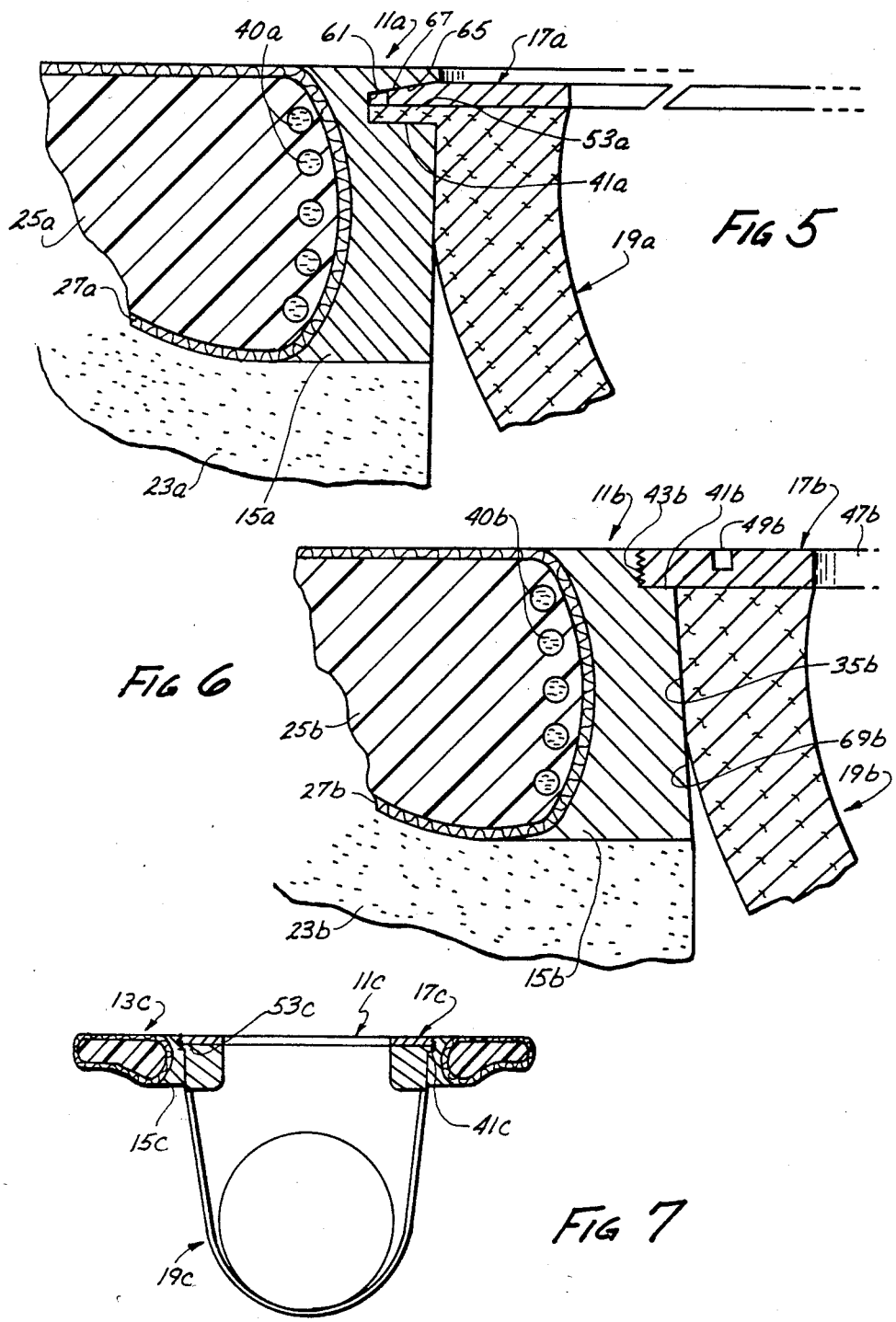

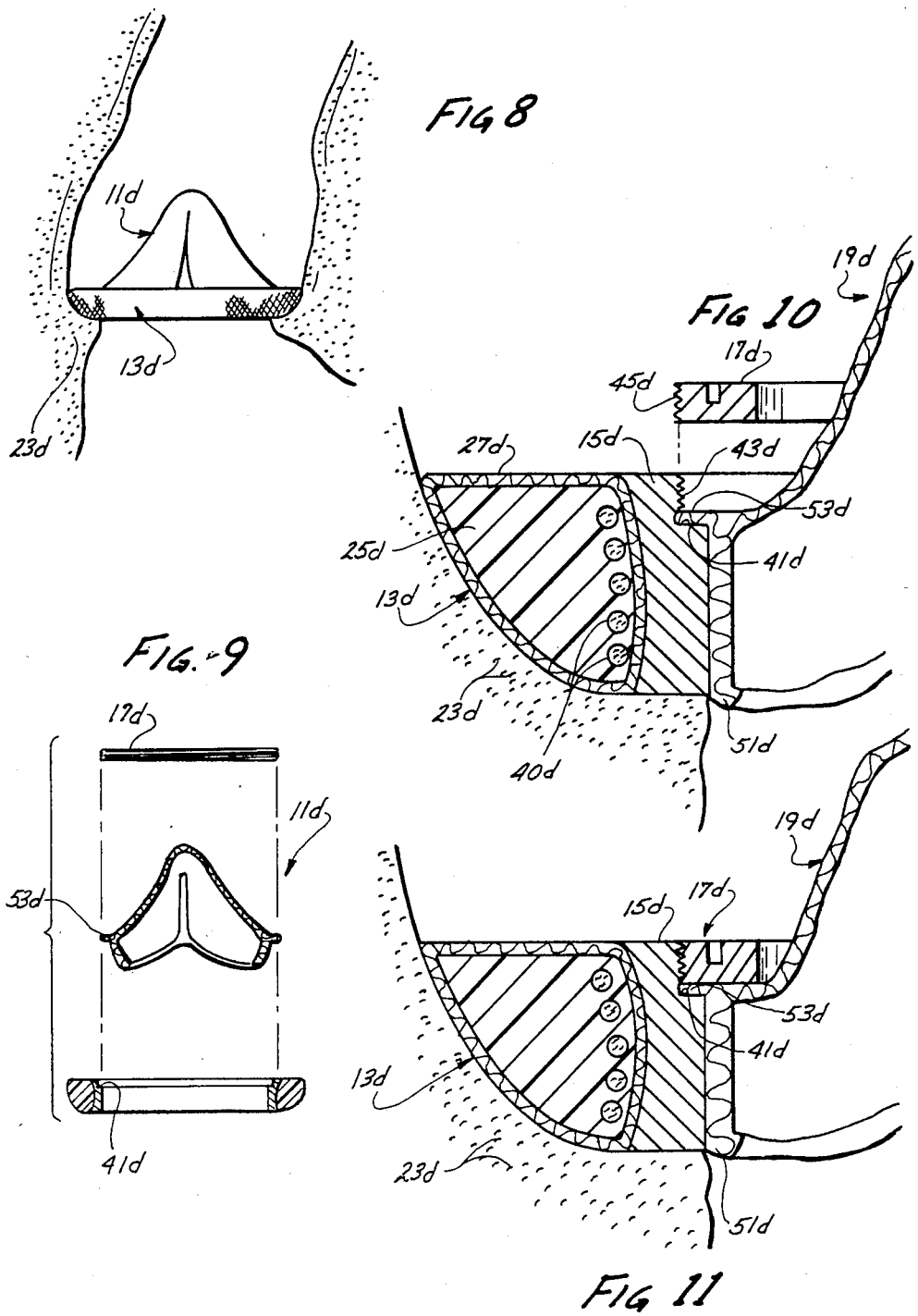

PROSTHETIC HEART VALVE ASSEMBLY

BACKGROUND OF THE INVENTION

Prosthetic heart valves have long been used to replace diseased or defective natural heart valves. One problem with prosthetic heart valves is that they tend to ear out. For example, in a prosthetic heart valve made of biological tissues, the tissues tend to progressively deteriorate due to fatigue or degenerative lesions. Accordingly, a second operation may be required to replace the prosthetic valve with a new one.

To facilitate the replacement surgery, an artificial annulus can be attached to the natural annulus, and a prosthetic valve can be releasably attached to the artificial annulus. Assemblies of this type are shown in Possis U.S. Pat. Nos. 3,997,923 and U.S. Pat. No. RE. 31,040 and Bedard U.S. Pat. No. 4,506,394.

The concept of removably attaching a prosthetic valve to an artificial annulus is desirable. However, there are problems associated with the prior art techniques for removably attaching the prosthetic valve to the artificial annulus.

For example, the Possis patents disclose the use of screw threads for threading the prosthetic valve into an artificial annulus. This requires rotation of the prosthetic valve, and this could lead to valve damage and makes angular orientation of the valve by the surgeon more difficult. The Bedard patent discloses attaching the prosthetic valve to an artificial annulus using sutures. This suturing process takes time to carry out thereby lengthening the surgery. The Bedard patent also suggests a snap-in connection between the artificial annulus and the prosthetic valve. However, this would require the application of force which might endanger any patient having a calcified annulus. Moreover, if the prosthetic valve were made resilient to allow for such a snap-in connection, there would be a danger of distortion and damage to the valve.

SUMMARY OF THE INVENTION

This invention provides a novel and advantageous way to removably mount a prosthetic valve on an artificial annulus. With this invention, the prosthetic valve can have any angular orientation desired by the surgeon, and the valve can be rapidly installed in the artificial annulus and rapidly removed therefrom. Furthermore, the surgery can be accomplished with a minimum of handling of the prosthetic valve, and the likelihood of the application of damaging forces to the prosthetic valve is materially reduced.

Many of the features of this invention can be embodied, for example, in an implantable device which removably mounts a prosthetic valve and in the implantable device in combination with the prosthetic valve. The implantable device may include a novel artificial annulus and a retaining ring releasably attachable to the artificial annulus for removably retaining the prosthetic valve. The retaining ring can be quickly and easily installed. The retaining ring is also removable to permit replacement of the prosthetic valve with another prosthetic valve.

The artificial annulus can advantageously include a fixation ring, which may be a suture ring, and a mounting ring. The fixation ring has an inner periphery defining an opening through the fixation ring and an outer periphery. The fixation ring is adapted to be affixed to the natural annulus of a patient.

The mounting ring has an inner peripheral surface defining an opening through the mounting ring. The mounting ring is coupled to the fixation ring, with the openings being in registry so that a prosthetic valve can be received in the opening of the mounting ring.

Means is provided at least partially on the mounting ring for releasably attaching the retaining ring to the mounting ring. Such means can take different forms and may include, for example, screw threads for threadedly attaching the retaining ring and the mounting ring. Alternatively, the attaching means may include a groove in the mounting ring, and in this event, the retaining ring may include a resilient ring receivable in the groove.

The retaining ring typically retains the prosthetic valve against moving in one direction out of the opening in the mounting ring. Means is provided for retaining the prosthetic valve against moving in the other direction out of the opening in the mounting ring. For example, such means may include a taper on the inner peripheral surface of the mounting ring and/or on a confronting surface of the prosthetic valve and/or cooperating shoulders on the mounting ring and the prosthetic valve.

To help provide a secure attachment, the mounting ring should be strong and preferably quite rigid. Typically, the mounting ring is more rigid than the fixation ring, which may be relatively soft to facilitate suturing of the fixation ring to body tissue. The mounting ring is preferably within the opening of the fixation ring and has a minimum radial dimension to provide a maximum flow area through the annulus.

The invention, together with additional features and advantages thereof, may best be understood by reference to the following description taken in connection with the accompanying illustrative drawing.

BRIEF DESCRIPTION OF THE DRAWING

FIG. 1 is a sectional view showing one form of prosthetic heart valve assembly of this invention implanted in the mitral position with the heart valve assembly being illustrated in elevation.

FIG. 2 is an exploded isometric view of the heart valve assembly.

FIG. 3 is an enlarged, fragmentary sectional view illustrating a peripheral region of the heart valve assembly, with the retaining ring about to be installed.

FIG. 4 is a fragmentary, sectional view similar to FIG. 3 with the retaining ring installed.

FIGS. 5 and 6 are fragmentary, sectional views similar to FIG. 4 illustrating second and third embodiments, respectively, of prosthetic heart valve assemblies of this invention.

FIG. 7 is a sectional view illustrating the application of the features of this invention to a mechanical prosthetic heart valve assembly.

FIG. 8 is a sectional view showing an aortic prosthetic heart valve assembly of this invention.

FIG. 9 is an exploded elevational view partially in section of the heart valve assembly of FIG. 8.

FIGS. 10 and 11 are fragmentary sectional views through a peripheral region of the prosthetic heart valve assembly illustrating the installation of the retaining ring.

DESCRIPTION OF THE PREFERRED EMBODIMENTS

FIGS. 1-4 illustrate a mitral prosthetic heart valve assembly 11 which generally comprises a fixation ring in the form of a suture ring 13, a mounting ring 15, a retaining ring 17 and a prosthetic mitral heart valve 19. The suture ring 13 and the mounting ring 15 together form an artificial annulus 21.

The suture ring 13 can be of any construction which will enable it to be securely affixed to a natural annulus 23 or adjacent body tissue. For example, it may comprise a relatively soft plastic core 25 covered with a suitable cloth 27, such as a Dacron cloth. The suture ring 13 has an outer periphery 29 and an inner periphery 31 which define an opening 33 through the suture ring 13. Although various constructions are possible, in this embodiment the inner periphery 31 is curved convexly in axial cross section as shown in FIG. 3.

The mounting ring 15 is a thin, essentially rigid, annular member of metal, such as a biocompatible stainless steel, or suitable plastic material. The mounting ring 15 has an inner peripheral surface 35 defining an opening 37 through the mounting ring.

The mounting ring 15 can be coupled to the suture ring 13 in various different ways and in different locations so long as the openings 33 and 37 are in appropriate registry so that the prosthetic valve 19 can be received in the opening 37. In this embodiment, the mounting ring 15 is mounted in the opening 33. In this regard, the mounting ring 15 has an outer peripheral surface 39 which is concave as viewed in axial section and which conforms to the inner periphery 31 of the suture ring 13. The suture ring 13 can be coupled to the mounting ring 15 and retained thereon by threads 40 of the suture ring 13 wound around the mounting ring or in any other suitable manner.

The peripheral surface 35 in this embodiment is essentially cylindrical. However, a shoulder 41 is formed near the upper end of the mounting ring 15, and screw threads 43 lead to the shoulder 41.

The retaining ring 17 has external screw threads 45 which cooperate with the threads 43 to permit the retaining ring to be screwed into the upper end of the mounting ring 15. Although various constructions are possible, in this embodiment, the retaining ring 17 projects radially inwardly for a short distance into the opening 37.

The retaining ring 17 is rigid and is constructed of a biocompatible metal or plastic and has a large central opening 47. Sockets 49 are provided in the upper surface of the retaining ring 17 to facilitate turning of the retaining ring into the threads 43.

The valve 19 may be of essentially conventional construction, except that it includes a relatively rigid base 51 having a peripheral flange or shoulder 53. The base 51 may be made rigid by a suitable metal or plastic frame member covered by a suitable fabric. The valve 19 also includes three commissures 55 (only two being shown in FIG. 2) and valve leaflets 57 of biological tissue or other suitable material.

In use, the natural mitral heart valve is removed, and the artificial annulus 21 is sutured to the natural annulus 23 using known surgical techniques, with the peripheral surface 35 of the mounting ring 15 being essentially flush with the opening defined by the natural annulus 3. Next, the valve 19 is inserted into the opening 37 in the desired angular orientation until the flange 53 rests on the shoulder 41. The retaining ring 17 is then threadedly attached to the mounting ring 15 to tightly clamp the flange 53 between the retaining ring and the shoulder 41. With this construction, the retaining ring 17 prevents the valve from moving upwardly out of the opening 37, and the flange 53 and the shoulder 41 cooperate to prevent the valve from moving downwardly out of the opening 37.

If it becomes necessary to replace the valve 19, the retaining ring 17 is unscrewed from the mounting ring 15, and the valve 19 can be lifted upwardly out of the opening 37. The valve 19 is then replaced with another prosthetic valve, and the new prosthetic valve is retained on the mounting ring 15 as described above.

FIGS. 5 and 6 show heart valve assemblies 11a and 11b, respectively, which are identical in all respects not shown or described herein to the heart valve assembly 11. Portions of the heart valve assemblies 11a and 11b corresponding to portions of the heart valve assembly 11 are designated by corresponding reference numerals followed by the letters "a" and "b", respectively.

The primary difference between the heart valve assemblies 11a and 11 is that the former has a resilient split retaining ring 17a provided in an annular groove 61 of the mounting ring 15a. Because the retaining ring 17a is a split ring, it can be radially compressed to permit it to be inserted into the groove 61 whereupon the resilience of the retaining ring causes it to expand into the groove and retain the flange 53a against the shoulder 41a. The use of the resilient split retaining ring 17a has the advantage of reducing the likelihood of the application of torsional forces to the heart valve assembly as a result of insertion and removal of the retaining ring.

If it is desired to have the retaining ring 17a clamp the flange 53a against the shoulder 41a, the groove 61 and the upper surface of the retaining ring 17a can be formed with cooperating inclined surfaces 65 and 67. As the retaining ring 17a expands radially outwardly due to its resilience upon being inserted into the groove 61, the inclined surface 65 acts like a cam to cam the retaining ring 17a downwardly against the flange 53a.

The heart valve assembly 11b is identical to the heart valve assembly 11, except that, in the former, the inner peripheral surface 35b and a confronting surface 69 of the valve 19b are tapered sufficiently to retain the valve against moving downwardly through the mounting ring 15. The confronting surface 69 is made sufficiently rigid to serve this purpose. In addition, the valve 19b has no flange 53b.

FIG. 7 shows a prosthetic heart valve assembly 11c which is identical to the prosthetic heart valve assembly 11, except that the valve 19c is a mechanical ball valve rather than a leaflet valve. Portions of the prosthetic valve assembly 11c corresponding to portions of the valve assembly 11 are designated by corresponding reference numerals followed by the letter "c." Except for the provision of the flange 53c, the valve 19c may be of conventional construction.

FIGS. 8-11 show a prosthetic valve assembly 11d which is identical to the valve assembly 11, except that the former is an aortic valve. Portions of the valve assembly 11d corresponding to portions of the valve assembly 11 are designated by corresponding reference numerals followed by the letter "d."

The suture ring 13d is shaped to conform to the tissue of the natural aortic annulus 23d, and as such, the suture ring 13d has a different configuration from the suture ring 13. In addition, the valve 19d has a relatively rigid flange 53d above its base 51d which rests on the shoulder 41d. In use, the threaded retaining ring 17d clamps the flange 53d against the shoulder 41d.

From the foregoing, it is apparent that the features of this invention are applicable to leaflet valves and mechanical valves and valves usable at various different locations within the heart. The various retaining members, including the threaded retaining member and the split ring retaining member, can be used with mechanical and leaflet valves, as well as valves for any position within the heart.

Although exemplary embodiments of the invention have been shown and described, many changes, modifications and substitutions may be made by one having ordinary skill in the art without necessarily departing from the spirit and scope of this invention.

We claim:

1. An implantable device for removably mounting a prosthetic valve, said implantable device comprising:
    a fixation ring having an inner periphery defining an opening through the fixation ring and an outer periphery and adapted to be affixed to the natural annulus of a patient;
    a mounting ring having an inner peripheral surface defining an opening through the mounting ring, said mounting ring being coupled to the fixation ring with said openings being in registry whereby a prosthetic valve can be received in said opening of the mounting ring;
    a retaining ring separate from the prosthetic valve so that when a prosthetic valve is received in said opening of the mounting ring the prosthetic valve can be angularly oriented independently of the retaining ring;
    means at least partially on said mounting ring for releasably attaching said retaining ring to the mounting ring so that the retaining ring can retain the prosthetic valve against moving in one direction out of the opening when the prosthetic valve is received in said opening of the mounting ring and the retaining ring can be removed to permit replacement of the prosthetic valve with another prosthetic valve;
    means for use in retaining the prosthetic valve against moving in another direction out of the opening in the mounting ring when the prosthetic valve is received in said opening of the mounting ring; and
    said retaining ring is annular, has an axis and is thin in the direction of said axis.

2. A device as defined in claim 1 wherein said attaching means includes threads on said retaining ring and on the mounting ring whereby the retaining ring is releasably attachable to the mounting ring and can be rotated without rotating the prosthetic valve.

3. A device as defined in claim 1 wherein said attaching means includes a groove in the mounting ring and the retaining ring includes a resilient ring receivable in said groove.

4. A device as defined in claim 1 wherein said retaining means includes said inner peripheral surface of the mounting ring being tapered.

5. A device as defined in claim 1 wherein said retaining means includes a shoulder on said mounting ring engageable with the prosthetic valve when the prosthetic valve is received in said opening of the mounting ring.

6. A device as defined in claim 1 wherein said mounting ring is more rigid than the fixation ring.

7. A device as defined in claim 1 wherein the mounting ring is within the opening of the fixation ring.

8. A device as defined in claim 5 wherein said attaching means includes a groove in the mounting ring and the retaining ring includes a resilient ring receivable in said groove.

9. A device as defined in claim 8 wherein the mounting ring is within the opening of the fixation ring.

10. A device as defined in claim 5 wherein said attaching means includes threads on said retaining ring and on the mounting ring whereby the retaining ring is releasably attachable to the mounting ring.

11. A valve assembly as defined in claim 1 wherein said retaining means is at least partially on said mounting ring.

12. A prosthetic heart valve assembly comprising:
    a fixation ring having an inner periphery defining an opening through the fixation ring and an outer periphery and adapted to be affixed to the natural annulus of a patient;
    a mounting ring having an inner peripheral surface defining an opening through the mounting ring, said mounting ring being coupled to the fixation ring with said openings being in registry whereby a prosthetic valve can be received in said opening of the mounting ring;
    a prosthetic valve receivable in said opening of the mounting ring;
    a retaining ring;
    means at least partially on said mounting ring for releasably attaching said retaining ring to the mounting ring so that the retaining ring can retain the prosthetic valve against moving in one direction out of the opening in the mounting ring when the prosthetic valve is received in said opening and the retaining ring can be removed without removing the prosthetic valve to permit replacement of the prosthetic valve with another prosthetic valve; and
    means for retaining the prosthetic valve against moving in another direction out of the opening in the mounting ring.

13. A valve assembly as defined in claim 12 wherein said attaching means includes threads on said retaining ring and on the mounting ring whereby the retaining ring is releasably attachable to the mounting ring.

14. A valve assembly as defined in claim 12 wherein said attaching means includes a groove in the mounting ring and the retaining ring includes a resilient ring receivable in said groove.

15. A valve assembly as defined in claim 12 wherein said retaining means includes said inner peripheral surface of the mounting ring and a confronting surface of the prosthetic valve being tapered.

16. A valve assembly as defined in claim 12 wherein said retaining means includes cooperating shoulders on the mounting ring and the prosthetic valve.

17. A valve assembly as defined in claim 12 wherein the mounting ring is within the opening of the fixation ring and is more rigid than the fixation ring.

* * * * *